United States Patent [19]

Giaramita

[11] Patent Number: 5,004,417

[45] Date of Patent: Apr. 2, 1991

[54] COLOR DENTAL KIT AND METHOD OF USE

[76] Inventor: Michael Giaramita, 7000 Bay Pkwy., Apt. 6H, Brooklyn, N.Y. 11204

[21] Appl. No.: 243,415

[22] Filed: Sep. 12, 1988

[51] Int. Cl.$^5$ .............................................. A61C 19/10
[52] U.S. Cl. ..................................................... 433/26
[58] Field of Search .................... 433/26; 434/84, 391; 206/1.7, 81, 371, 575

[56] References Cited

U.S. PATENT DOCUMENTS

| | | | |
|---|---|---|---|
| 1,709,066 | 4/1929 | Field | 433/26 |
| 1,957,816 | 5/1934 | Braeg | 206/81 |
| 3,492,143 | 1/1970 | Oberg | 434/84 |

*Primary Examiner*—Cary E. Stone
*Attorney, Agent, or Firm*—Emmanuel J. Lobato; Robert E. Burns

[57] ABSTRACT

A color dental kit and method of specifying and illustrating coloring of synthetic dental elements such as individual teeth, crowns and the like to be made synthetically by imaging the individual teeth or crowns on a sheet of paper divided into light and dark incisal color tones. The color is effected with color pencils having a soft lead of the colors corresponding to gingival and incisal natural color shades. Some of the color pencils have leads for coloring specific color characteristics such as flaws including decalcification. The color pencils are provided in the color dental kit including therewith paper sheets on which imaging of the individual synthetic teeth and crowns is effected and the images are manually colored with the pencils as desired. These colored images provide positive dentition communication between and among dentists, patients and dental laboratory technicians.

9 Claims, 2 Drawing Sheets

COLOR DENTAL KIT AND METHOD OF USE

BACKGROUND OF THE INVENTION

This invention relates generally to the making of synthetic teeth, dental elements such as crowns and the like and more particularly to a color dental kit and a method of use of the kit for reproducing the appearance of natural dentition for communication between dentist, a patient and lab technicians.

Dental restorations have heretofore presented problems for dentists in communicating with lab technicians with respect to guiding the dental laboratory with respect to shade definition of colors desired on synthetic teeth, crowns, inlays, onlays and veneers and the like. Several techniques are employed by dentists for communicating their needs to dental laboratories. In some instances patients must visit the laboratory or the lab technician confers with the patient and the dentist which is generally a cumbersome method since laboratories are not readily accessible to the patients. Other dentists will take a photograph and transmit this to the laboratory. The most common method is by drawing the tooth and describing the color characteristics. The latter technique may appear to be a practical way for the dentist and lab to communicate but it is not effective because the communication is attempting to identify a highly complex color medium with a black/blue pen and white paper. The dentist then the lab may perceive the colors and tones of a color movie of a black and white television set for the communications are far from perfect. Another method is the use of a shade guide in which tooth simulations are made of porcelain on which the appearance of natural dentition and all lighting condition is attempted. The elements provide the physical color by which the dentist and lab technician can identify the color shades desired in a synthetic tooth or crown or the like.

SUMMARY OF THE INVENTION

According to the present invention a color dental kit having color pencils is used by a dentist in specifying color characteristics of individual synthetic teeth, crowns, overlays, inlays, veneers and the like. The color pencils have a soft lead. The colors include color shades corresponding to gingival and incisal shades existing in nature. The kit includes pencils for representing specific flaws or color areas on the patients tooth such as a white color for representing a decalcified area. These particular color pencils include black, grey, brown, pink, yellow, orange, violet, green and blue.

The kit includes sheets of paper on which teeth are already imaged or without such images. The free-drawn teeth avoid any need for a dentist to image a tooth and color it according to the desired color. The dentist simply colors the imaged tooth as desired. The sheets of paper in the kit also include sheets divided into light and dark incisal tones. The color kit is used for graphically describing and illustrating the colors of individual synthetic dental elements to be made. The dentist may image the tooth himself on the paper or use the predrawn images of teeth and he colors them with the individual pencils so that the colored image has the tones of natural teeth. The laboratory receiving the colored image can then see exactly what color shades are to be employed in the making of a synthetic element and is provided with an optimum shade guide.

BRIEF DESCRIPTION OF THE DRAWINGS

The colored dental kit and method according to the invention can be best understood by reference to the following description, claims and appended drawings in which:

DESCRIPTION OF THE PREFERRED EMBODIMENT

Figure 1:
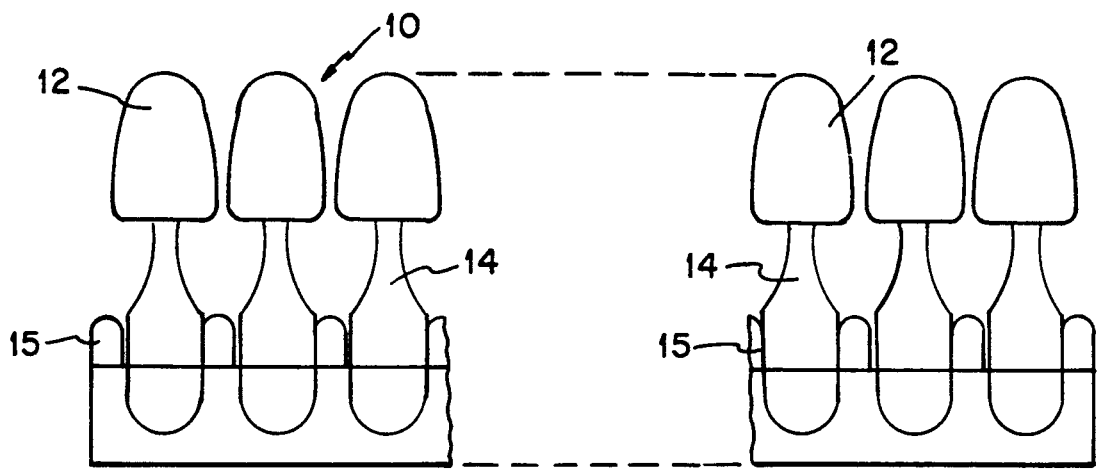
FIG. 1 is a fragmentary elevation view of a shade guide according to the prior art.

A prior art shade guide 10 is illustrated in FIG. 1. The guide is provided with a plurality of porcelain shade guide elements 12 removably mounted in a holder 14 and identified with indicia 15. The guide elements 12 are provided with color shades which can be matched with the teeth of the patient by a dentist and by which the particular element color shade guide identifies for a laboratory the shade of the tooth, crown, onlay, inlay, and veneer and the like to be made for the dentists by the laboratory.

Figure 2:
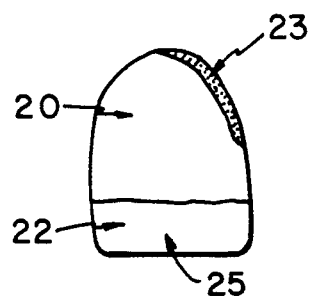
FIG. 2 is an image of a tooth for explanatory use of the prior art.
Figure 4:
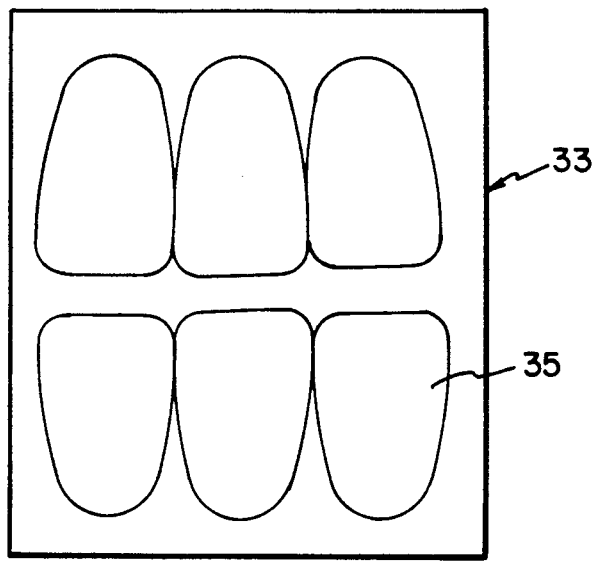
FIG. 4 is a plan view of a diagram of a sheet of paper of a kit according to the invention illustrating predrawn teeth.

The basic shades of a human tooth are illustrated graphically in the image of a tooth in FIG. 2. A natural tooth has a gingival tone over an area 20 that in most cases covers about two thirds of the tooth measured from the gum line. An incisal tone 22 is located at the incisal edge of the tooth as illustrated in FIG. 2. A tooth can have unique characteristics including color or defects and these may constitute white spots indicative of a decalcified area 23. Translucent hues ranging from brown, yellow and grey highlights can be found in tooth areas, for example in the area 25.

In order for a dentist to communicate his needs for shades on the synthetic teeth and the like to be made in a laboratory a highly accurate shade guide is required. According to the invention a color pencil kit thirty is provided with a plurality of color pencils as later herein described.

The kit includes sheets of paper 33 which may be blank or have one or more pre-drawn teeth images 35. The sheets may be blank and are preferably provided as a pad divided into light and dark incisal tones.

Communications between a dentist and a dental laboratory and the technicians thereof in the area of custom colored synthetic teeth or other synthetic structures such as crowns, onlays, inlays and veneers present a problem. In many instances standard stock colors are perfectly all right for use on posterior teeth. On such teeth the custom shades are not critical. With respect to anterior teeth there is no existing easy and practical way for the dentist to relay the matching specification of teeth to a dental lab, particularly when there exist strong unique color characteristics.

Figure 5:
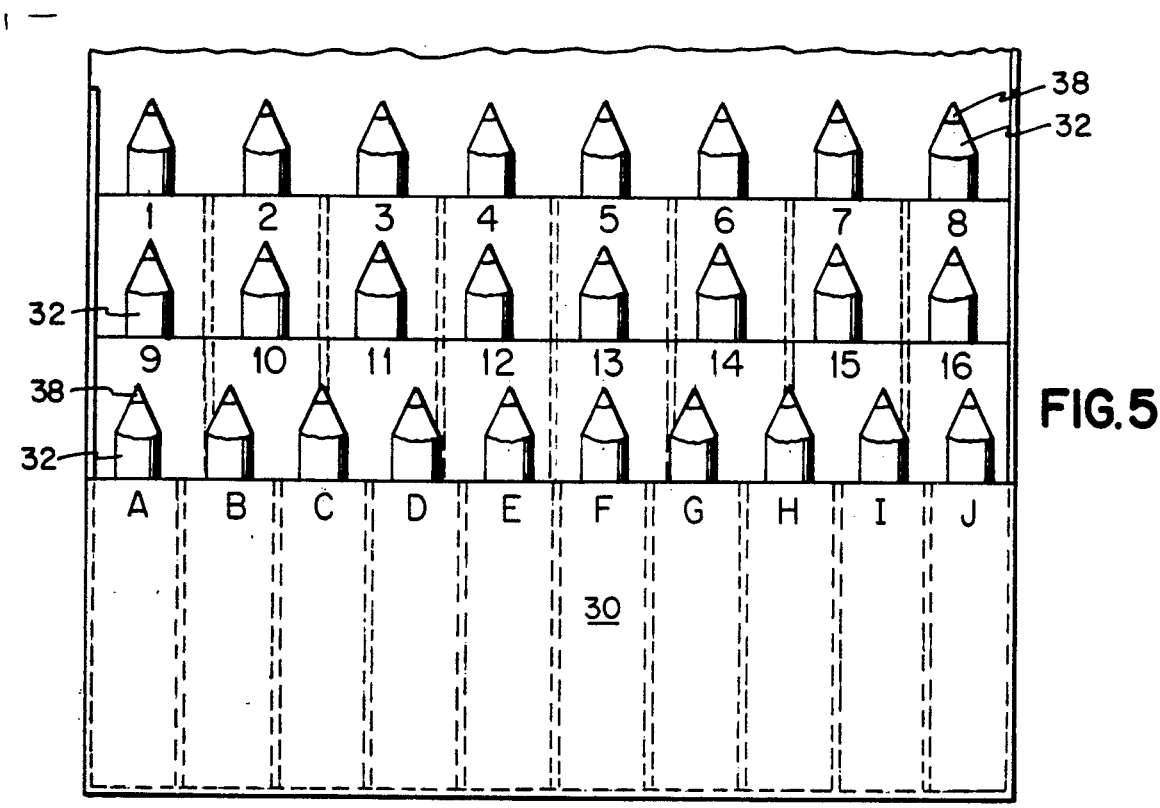
FIG. 5 is the fragmentary elevation view of a kit according to the invention.

According to the kit 30 of the present invention the color pencils in the kit are provided with a tip 32 having a lead 38 which is soft. The kit comprises sixteen color pencils with soft leads which makes the colors blendable. These colors can be blended to match standard body shades and are illustrated in FIG. 5. The top two rows of pencils illustrated in FIG. 5 are numbered 1-16 inclusive and constitute the gingival shades or colors for blending to establish the gingival shades. The lower row has the pencils designated A-J inclusive and face pencils are used for particular characteristics. The colors thereof are as follows:

A—White
B—Black
C—Grey
D—Brown
E—Pink
F—Yellow
G—Orange
H—Violet
I—Green
J—Blue thus with these colors white can be used for illustrating decalcified areas, blue for transluscent spots and the different colors provide for illustrating the shades for illustrating flaws.

Figure 3:
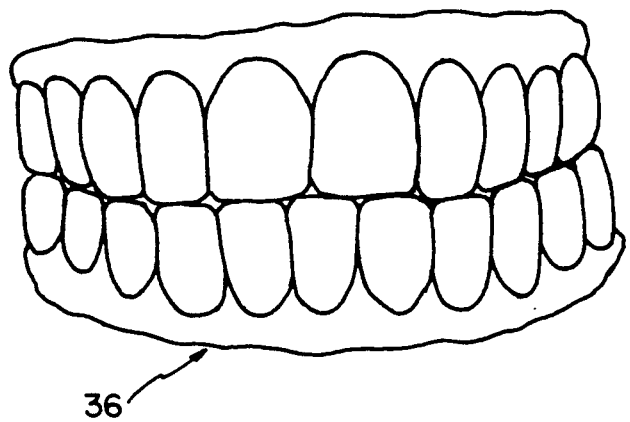
FIG. 3 is an elevation view of a diagram of anterior teeth for illustration of the invention.
Figure 6:
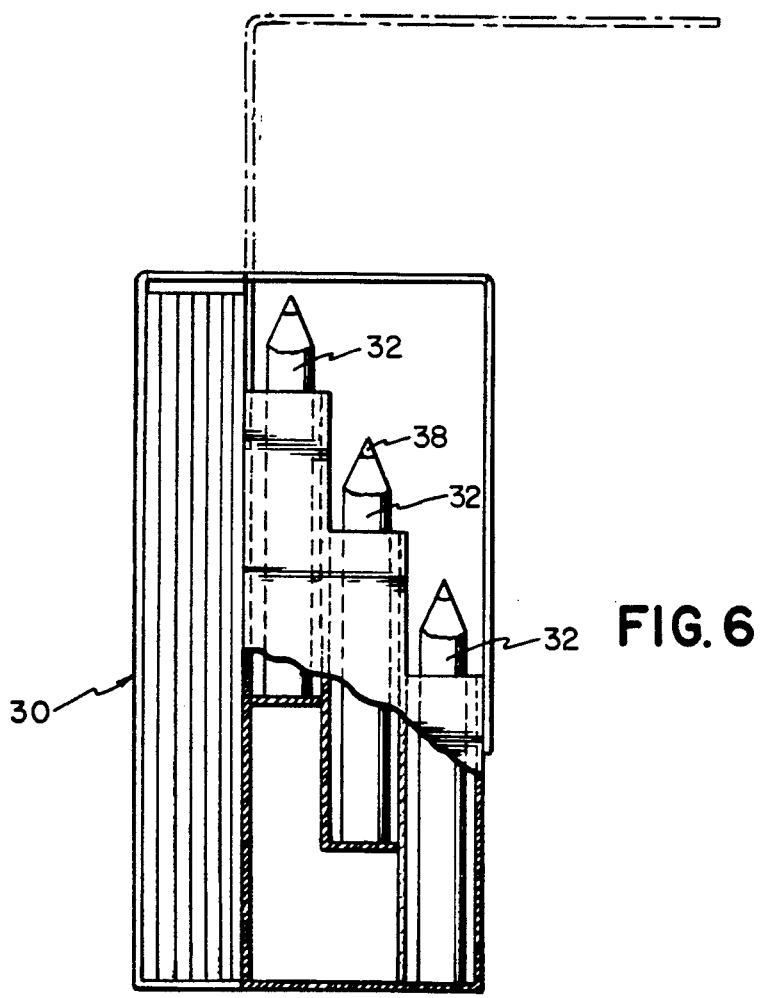
FIG. 6 is a fragmentary side elevation view pertinent section of the kit illustrated in FIG. 5.

The kit is illustrated in FIG. 6 with the lid open and a pad 50 is removably contained in kit 30. The pad has paper sheets divided into light and dark incisal tones with and without pre-drawn teeth as indicated heretofore. The dentist accordingly has the necessary tools for illustrating in detail to the laboratory teeth arrangements 36 such as illustrated in FIG. 3 on which the specific color shades can be detailed for illustrating the desired shades for the making of synthetic teeth and related dental elements.

Those skilled in the art understand that while soft lead pencils have been described as the color instruments, the term pencils is used generically and other instruments such as color crayons, colored chalks and the like may be used as the color instruments. It is necessary, however, that these color instruments are able to be used to make color images having the color tones of natural teeth. It is also understood that water colors can likewise be used according to the invention.

I claim:

1. A color dental kit for use in specifying color characteristics of individual synthetic teeth, dental elements such as crowns and the like comprising, a plurality of color pencils for coloring of an image of a synthetic tooth in gingival and incisal shades simulating those shades in nature, and including sheets of paper divided into light and dark incisal tones.

2. A kit for use in specifying color characteristics of individual synthetic teeth, dental elements such as crowns and the like according to claim 1, including sheets of paper having teeth pre-drawn thereon.

3. A kit for use in specifying color characteristics of individual synthetic teeth, dental elements such as crowns and the like according to claim 1, in which said pencils have a soft lead.

4. A kit for use in specifying color characteristics of individual synthetic teeth, dental elements such as crowns and the like according to claim 1, in which said pencils comprise gingival shades, incisal shades, shades for illustrating a decalcified area, and translucent hues to brown, yellow and grey highlights and pencils for unique characteristics comprising white, black, grey, brown, pink, yellow, orange, violet, green and blue.

5. A method for describing and illustrating the colors for individual synthetic teeth, dental elements such as crowns and the like to be made comprising, imaging on paper at least an individual tooth or crown to be made synthetically, coloring the tooth or crown image with color pencils having lead shades corresponding to the gingival and incisal color tones of natural teeth.

6. A method for describing an illustrating the colors of individual synthetic teeth, dental elements such as crowns and the like to be made according to claim 5, in which the paper on which said imaging is made is divided into light and dark incisal color tones.

7. A color dental kit for use in specifying color characteristics of individual synthetic teeth, dental elements such as crowns and the like comprising, a plurality of coloring implements for coloring of an image of a synthetic tooth in gingival and incisal shades simulating those shades in nature, and including sheets of paper divided into light and dark incisal tones.

8. A method for describing and illustrating the colors for individual synthetic teeth, dental elements such as crowns and the like to be made comprising, imaging on paper at least an individual tooth or crown to be made synthetically, coloring the tooth or crown image with coloring implements having coloring shades corresponding to the gingival and incisal color tones of natural teeth.

9. A method for describing and illustrating the colors of individual synthetic teeth, dental elements such as crowns and the like to be made according to claim 8, in which the paper on which said imaging is made is divided into light and dark incisal color tones.

* * * * *